US006261541B1

(12) United States Patent
Karpov et al.

(10) Patent No.: US 6,261,541 B1
(45) Date of Patent: Jul. 17, 2001

(54) SUNLESS TANNING EMULSIONS WITH DISAPPEARING COLOR INDICATOR

(75) Inventors: Inna Karpov, Germantown, TN (US); Elaine M. Morefield, Richmond, VA (US); Jamie S. Ross, Putnam, CT (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 08/977,023

(22) Filed: Nov. 24, 1997

Related U.S. Application Data

(60) Provisional application No. 60/032,024, filed on Nov. 25, 1996.

(51) Int. Cl.[7] .............................. A61K 7/42; A61K 7/44; A61K 9/00; A61K 7/00
(52) U.S. Cl. ............................ 424/59; 424/60; 424/400; 424/401
(58) Field of Search ................................. 424/59, 60, 400, 424/401

(56) References Cited

U.S. PATENT DOCUMENTS

| 4,434,154 | | 2/1984 | McShane ............................ 424/60 |
| 5,523,075 | * | 6/1996 | Fuerst et al. ........................ 424/59 |
| 5,626,839 | | 5/1997 | Scales-Medeiros ................. 424/59 |
| 5,700,452 | * | 12/1997 | Deckner et al. .................... 424/59 |

FOREIGN PATENT DOCUMENTS

| 94/26233 | * | 11/1994 | (WO) . |
| WO 94/26233 | | 11/1994 | (WO) .............................. A61K/7/00 |
| WO 95/28912 | | 11/1995 | (WO) .............................. A61K/7/42 |
| WO 96/14826 | | 5/1996 | (WO) .............................. A61K/7/42 |

OTHER PUBLICATIONS

Fishman, "Certified dyes", Happi, p. 28, Jan. 1995.*
"Concise Encyclopedia Chemistry", Walter de Gruyter, Berlin, New York, pp. 437 and 438, 1994.*

Derwent World Patent Index Abstract No. 96–255059, 1996.

L. Calvo, "Formulating Color Cosmetics Worldwide," *Cosmetics and Toiletries*, Feb. 1995, pp. 33, 34, 36 and 38.

H. M. Fishman, "Gleams Notions, Certified Dyes," *Happi*, Jan. 1995, p. 28.

* cited by examiner

*Primary Examiner*—Shelley A. Dodson
*Assistant Examiner*—Marina Lamm
(74) *Attorney, Agent, or Firm*—Robert A. Franks; Joseph T. Majka

(57) ABSTRACT

A colored, sunless tanning emulsion is disclosed which employs a water-soluble dye or a blend of water-soluble dyes whose color substantially disappears when the sunless tanning emulsion dries after it is spread on the skin and/or is rubbed out. The coloration in the sunless tanning emulsion enables the user to apply the emulsion more evenly to the skin, giving a smooth, uniform tan over the skin surface The colored, sunless tanning emulsion comprises:

a) at least one water-soluble dye that imparts a color other than white to the sunless tanning emulsion, such that when the emulsion dries after it is spread on the skin and/or is rubbed out, the color substantially disappears;

b) at least one sunless tanner;

c) at least one emulsifier; and d) sufficient water to form the colored emulsion; and optionally, e) one or more emollients, humectants, dry-feel modifiers, antimicrobial preservatives, thickening agents, antifoaming agents, antioxidants, chelating agents, sunscreen actives and fragrances as well as any other class of materials whose presence may be cosmetically, efficaciously or otherwise desirable.

20 Claims, No Drawings

SUNLESS TANNING EMULSIONS WITH DISAPPEARING COLOR INDICATOR

This application claims benefit of provisional application Ser. No. 60,032,024 filed Nov. 25, 1996.

BACKGROUND

Sunless tanners are products applied to the skin to provide a tan appearance, without exposure to the sun or other radiant energy sources, e.g. tanning beds and ulta-violet lamps. For optimum performance, sunless tanners should be applied evenly to provide a smooth, uniform tan over the skin surface. Unfortunately, a sunless tanner may be applied unevenly because it is difficult to see or visualize after being applied to the skin. Uneven applications may result in a cosmetically unattractive tan having streaks and/or spots. Further, once the sunless tanner is applied to the skin, the tan produced cannot be washed off since the tan is bound to the skin, and the user may need to wait one to two weeks for the uneven tan to wear off. Accordingly, an approach was sought to provide a sunless tanning emulsion which could be readily visualized and thus applied more evenly to the skin, yet would substantially disappear when dried and/or rubbed out on the skin.

SUMMARY OF INVENTION

It has been surprisingly and unexpectedly found that although the inclusion of a water-soluble dye to a sunless tanning emulsion can render the emulsion visually colored, that such coloration would substantially disappear when the colored emulsion dries after it is spread on the skin and/or is rubbed out.

Thus, in one embodiment, the present invention is directed towards a colored, sunless tanning emulsion comprising:

a) at least one water-soluble dye that imparts a color other than white to the colored emulsion, such that when the colored emulsion dries after it is spread on the skin and/or is rubbed out, the color substantially disappears;

b) at least one sunless tanner;

c) at least one emulsfier; and d) sufficient water to form the colored emulsion.

Preferably, the water-soluble dye is an External DC color or blend thereof, more preferably a blend or mixture of Ext DC violet #2, Ext DC red#33 and FDC Yellow #6, to give a brown color. Also preferred is that the sunless tanner is dihydroxyacetone (DHA). The amount of the water-soluble dye in the colored emulsion can range from about 0.00001 to about 0.5% by weight of the colored, emulsion or composition, preferably from about 0.0001 to about 0.2%, more preferably from about 0.001 to about 0.1%, most preferably from about 0.01 to about 0.05%. Also preferred is that the colored emulsion is an oil-in-water emulsion.

Optionally, the colored, sunless tanning emulsion can contain one or more emollients, humectants, dry-feel modifiers, preservatives, thickening agents, antifoaming agents, antioxidants, chelating agents, sunscreen actives, and fragrances as well as any other class of materials whose presence may be cosmetically, efficaciously or otherwise desirable.

In another embodiment, the present invention is directed towards a method for more uniformly tanning the skin comprising topically applying to the skin the colored, sunless tanning emulsion described above.

The present invention advantageously provides a colored, sunless tanning emulsion that enables the user to apply the emulsion more evenly to the skin, thus providing a more uniform and cosmetically acceptable tan.

Another advantage of the present invention is that it provides a method for more uniformly tanning the skin by topically applying to the skin a colored, sunless tanning emulsion which can be readily visualized as it is being applied to the skin and which substantially disappears when dried on the skin and/or rubbed out on the skin.

DETAILED DESCRIPTION OF THE INVENTION

In the present specification, the terms "emulsion" and "composition" can be used interchangeably. The emulsion of the present invention contains one or more water-soluble dyes, sunless tanning actives, emulsifiers and water; and may optionally contain one or more emollients, humectants, dry-feel modifiers, antimicrobial preservatives, thickening agents, antifoaming agents, antioxidants, chelating agents, sunscreen actives and fragrances as well as any other class of materials whose presence may be cosmetically, efficaciously or otherwise desirable.

Definitions and suppliers of the ingredients described in this section and in the following illustrative examples may be found in the CTFA Cosmetic Ingredient Dictionary, published by the Cosmetic, Toiletry and Fragrance Association, Inc., 1110 Vermont Avenue, NW, Wash. D.C. 20005, Third Edition 1982. Proportions are by percent weight.

Water Soluble Dyes

Certified dyes are synthetic organic coal tar derivatives which are manufactured so that each batch passes a Food & Drug Administration (FDA) purity inspection. If approved by the FDA, these dyes are certified for use in foods, drugs, cosmetics (FDC colors), drugs and foods only (DC colors), or in topically applied drugs and cosmetics (External DC colors). Certified dyes can be water soluble or lakes. Lakes are organic pigments prepared by precipitating a soluble dye on a reactive or absorbent stratum which is an essential part of the pigment's composition. Most lakes are aluminum, barium or calcium derived. These insoluble pigments are used mostly in makeup products, either powders or liquids, when a temporary color is desired that will not stain the skin (as oil-soluble dyes tend to do). The lakes are used in these products along with inorganic colors such as iron oxide, zinc oxide and titanium dioxide (the whitest white pigment).

Water soluble, certified dyes are used mostly in color products, not skin or hair, although it is possible to make a temporary hair color rinse using only certified dyes. When incorporating these dyes in an emulsion, they will be soluble in the external water phase in an oil/water system. It is useful to know the solubility properties of the certified dyes in various solvents and their stability to reactive chemicals. Table I lists some of the currently available water soluble certified dyes.

TABLE I: WATER-SOLUBLE DYES

FDC Blue #1
FDC Blue #2
FDC Green #3
FDC Red #3
FDC Red #4
FDC Yellow #5
FDC Yellow #6

DC Green #5

DC Red #22

DC Red #28

DC Red #33

DC Yellow #10

Ext DC Violet #2

Ext DC Yellow #7

DC Green #8

DC Orange #4

DC Yellow #8

When using these dyes in an emulsion, they can be added drop by drop from a prepared solution to obtain or to match a particular shade. Or the dyes can be premixed with water or a portion of the water soluble (i.e. aqueous phase) to a certain color and then added to the product. Below are some suggestions for premixing or blending two or more of these dyes to obtain a particular shade (Table II).

TABLE II

DYE COMBINATIONS

|  | Pink | Amber | Lime | Olive Green | Beige | Purple | Brown | Dark Brown |
|---|---|---|---|---|---|---|---|---|
| FDC Red #3 | 95 | — | — | — | — | — | — | — |
| FDC Yellow #5 | 5 | — | 99 | — | 88 | — | — | — |
| DC Orange #4 | — | 93 | — | 5 | 10 | — | — | 50 |
| DC Green #5 | — | 7 | — | 70 | — | — | — | 38 |
| FDC Blue #1 | — | — | 1 | — | 2 | — | — | — |
| DC Yellow #10 | — | — | — | 25 | — | — | — | — |
| DC Red #28 | — | — | — | — | — | — | — | 12 |
| Ext DC Violet #2 | — | — | — | — | — | 95 | 22 | — |
| Ext DC Red #33 | — | — | — | — | — | 5 | 1 | — |
| FDC Yellow #6 | — | — | — | — | — | — | 77 | — |

The water-soluble color dye can also be a natural color, such as carmel color.

The colored, sunless tanning emulsion should contain the water-soluble color dye (color indicator) in an amount sufficient to enable the emulsion to be readily visualized (i.e. colored) when initially applied to the skin, such that when the emulsion dries after being spread on the skin and/or is rubbed out using one's hand and/or fingers, the color substantially disappears. One or more water-soluble dyes can be employed in the emulsion in an amount ranging from about 0.00001 to about 0.5% by weight of the colored, emulsion or composition, preferably from about 0.0001 to about 0.2%, more preferably from about 0.001 to about 0.1%, most preferably from about 0.01 to about 0.05%.

Also preferred is that the water-soluble color dye is a blend or mixture of Ext DC violet #2, Ext DC red#33 and FDC Yellow #6 to give a brown color. More preferably the weight ratio of the Ext DC violet #2:Ext DC red#33:FDC Yellow #6 is respectively about 22:1:77. In preparing the above blend, the Ext DC violet #2 and Ext DC red#3 can initially be mixed in a ratio of about 95:5 (Ext DC violet #2:Ext DC red#3) to give a purple blend. This purple blend subsequently can be mixed with the FDC Yellow #6 in a ratio of about 3:10 (purple blend:FDC Yellow #6) to give a light brown color. The brown color of the blend can be made more intense or darker by increasing the amounts of each dye in the blend (e.g. 6:20 and 9:30) while maintaining the same proportion of each dye ingredient.

Sunless Tanning Actives

For purposes of the present patent specification, the terms "sunless tanning active or agent," "sunless tanner," "skin tanner," "skin tanning active or agent" and "self tanning agent" can be used interchangeably. A sunless tanner refers to any compound or material which imparts a tan or brown appearance to the skin by exposure to the sunless tanner, without the need to expose the skin to the sun or other radiant energy sources. Representative sunless tanners include, but are not limited to dihydroxyacetone (DHA) and botannical extracts of plants such as the silver birch (*Betulla alba*), or *Eclipta alba* which contains flavonoids known as wedelolactone, demethylwedelolactone and mixtures thereof. Such botannical sources are described in U.S. Pat. No. 5,559,146. One particular formulation is known as Mahakanni STLC, a self-tanning liposome concentrate whose active ingredient(s) are believed to be derived from *Eclipta alba,* as described in Faking it without DHA, Soap, Perfumery and Cosmetics, September 1996, pp. 33–35. Such botannical extracts can be used alone or in conjunction with DHA. For example, when DHA is used in conjuction with Mahakanni STLC, representative ratios include about 3% DHA: 4% Mahakanni STLC; and 4% DHA: 2% Mahakanni STLC. The amount of the sunless tanner in the emulsion can range from about 0.1 to about 8 weight %, preferably from about 2 to about 7%, more preferably from about 3 to about 6%.

Emulsions/Emulsifiers

A stable emulsion is a mixture of two immiscible liquids, i.e. liquids that are not mutually soluble, but in the presence of an emulsifier, are mechanically agitated and shaken so thoroughly together that one liquid forms drops in the other one, giving the mixture the appearance of a homogeneous liquid. Liquids can include materials which are solid or solid-like at room temperature, but will liquify at a higher temperature during processing. The presence of an emulsifier enables one of the immiscible liquids to remain in a continuous form, while allowing the other immiscible liquid to remain in a dispersed droplet form. Thus, one function of an emulsifier, a stabilizing compound, is to assist in the production of a stable emulsion. A secondary function of emulsifiers is to provide a thickening or "bodying" to an emulsion. Typically, emulsifiers are molecules with non-polar and polar parts that are able to reside at the interface of the two immiscible liquids. As used herein in reference to the water-in-oil emulsifiers, the term "HLB value" means the hydrophile/lipophile balance. The HLB value has been used by those skilled in the emulsion art for selecting emulsifiers useful for preparing, inter alia, water-in-oil emulsions. See U.S. Pat. No. 4,177,259 and references cited therein.

An oil-in-water (o/w) emulsion is a mixture where oil droplets (the discontinuous phase) are dispersed in water (the continuous aqueous phase). A water-in-oil (w/o) emulsion is a mixture where water droplets (the discontinuous phase) are dispersed in oil (a continuous oil phase). Preferably the composition of the present invention is an oil-in-water emulsion where the oil-soluble actives are dispersed in the oil phase, prior to mixture with the water phase. The type of emulsion, oil-in-water (o/w) or water-in-oil (w/o) formed, is sometimes determined by the volume ratio of the two liquids provided the ratio is sufficiently high. For example, with 5% water and 95% oil (an o/w phase ratio of 19), the emulsion likely will become w/o. For moderate ratios (<3), the type of emulsion is decided by several factors, such as order of addition or type of emulsifier. One liquid slowly added to a second liquid with agitation usually results in the second liquid being the continuous phase. Another factor is preferred solubility of the emulsifier, the phase in which the emulsifier is soluble most probably is continuous.

More complex emulsions such as double emulsions are formed where an emulsion is dispersed in an continuous phase. For example, in an oil in-water-in oil (o/w/o) emulsion, the water in a continuous water phase containing dispersed oil droplets, are themselves dispersed in a continuous oil phase. Similarly, in a water-in oil-in water (w/o/w) emulsion, the oil in a continuous phase containing dispersed water droplets, are themselves dispersed in a continuous water phase. These more complex emulsions find use as a system for slow delivery, extraction, etc.

Typical suitable emulsifiers having an HLB value about 1 to about 7 include sorbitan monooleate, sorbitan sesquioleate, sorbitan isostearate, sorbitan trioleate, PEG-22/dodecyl glycol copolymer, PEG-45/dodecyl glycol copolymer, polyglyceryl-3-diisostearate, polyglycerol esters of oleic/isostearic acid, polyglyceryl-4 oleate, polyglyceryl-4 oleate/PEG-8 propylene glycol cocoate, oleamide DEA, sodium glyceryl oleate phosphate and hydrogenated vegetable glycerides phosphate.

Other emulsifiers useful in the present invention may be non-ionic, liquid or solid at room temperature and preferably compatible, i.e., soluble and stable with emollients. Preferred emulsifiers have a HLB value of less than about 5, e.g., sorbitan sequioleate (HLB value is 3.7), sorbitan monooleate (HLB value is 4.3) and sorbitan trioleate (HLB value is 1.8). Other preferred emulsifiers include polymeric emulsifiers such as copolymers of $C_{10}$–$C_{30}$ alkyl acrylates and one or more monomers of acrylic acid or methacrylic acid, also known as Pemulen® TR1 and TR2, trademark of B. F. Goodrich Inc., Cincinnati, Ohio. Other emulsifiers include sorbitan esters such as sorbitan isostearate available as Crill 6, tradename of Croda Inc. of New York, N.Y.; polyglyceryl-3 distearate available as Cremophor, tradename of BASF, Parsippany N.J.; Carbomer, which is a homopolymer of acrylic acid crosslinked with an allyl ether of sucrose, available as Carbopol 941, tradename of B. F. Goodrich, Cleveland, Ohio; Promulgen® G, a non-ionic emulsifier composed of a stearyl alcohol and ethyoxylated cetearyl alcohol [CTFA adopted name: Stearyl alcohol (and) Ceteareth-20], trademark of Amerchol Corporation, Edison, N.J.; and surfactants such as such as DEA-cetyl phosphate, also known as Amphisol®, trademark of Bemel Chemical Co., Englewood, N.J.; Brij®52 surfactant, a polyoxyethylene (2) cetyl ether [INCI Name Cereth-2], trademark of ICI Americas Inc., Wilmington, Del.; and Brij®56 surfactant, a polyoxyethylene (10) cetyl ether [CTFA Name: Ceteth-10], trademark of ICI Americas Inc.

During preparation of the emulsion, an acid or a base may be added to adjust the pH of one or more ingredients, e.g. to adjust the viscosity of a polymeric thickener in the emulsion. For example, triethanolamine, a base, can be used to increase the pH of the water phase and consequently, modify the desired viscosity of the emulsion. The emulsion can have a pH of about 2.5 to about 7, preferably from about 3 to about 5.5.

Conveniently, one or more emulsifiers can be used in the compositions of the present invention in amounts ranging from about 0.05 to about 20 weight percent of emulsion, preferably from about 0.1 to about 15%, more preferably from about 5 to about 10%.

Water

Water is employed in amounts effective to form the emulsion. For hydrophilic or water-loving ingredients, e.g., emulsifiers, emolients, etc., the amount of water should be sufficient to at least solubilize these ingredients. For hydrophobic or water-repelling ingredients, the water should be employed in amounts to serve as the continuous phase of the emulsion, at least for oil-in water emulsions. Thus, the amount of water in the emulsion or composition can range from about 2 to 95 weight %, preferably from 50 to 85%. Preferably the water is filtered and/or distilled, although unfiltered tap water can also be used.

Emollients

An emollient is an oleaginous or oily substance which helps to smooth and soften the skin, and may also reduce its roughness, cracking or irritation. Typical suitable emollients include mineral, oil, having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa., isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be use in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the emulsion in an amount ranging from about 1 to about 50 weight %, preferably about 3 to about 10%.

Humectants

A humectant is a moistening agent that promotes retention of water due to its hygroscopic properties. Suitable humectants include glycerin, polymeric glycols such as poyethylene glycol and polypropylene glycol, and sorbitols such as sorbitol solution. One or more humectants can optionally be included in the emulsion in amounts from about 1 to 20 weight %, more preferably from about 3 to about 15 weight %.

Dry-Feel Modifier

A dry-feel modifier is an agent which when added to the sunless tanning emulsion, imparts a "dry feel" to the skin when the emulsion dries. Dry feel modifiers can include starches, talc, kaolin, chalk, zinc oxide, silicone fluids, inorganic salts such as barium sulfate and sodium chloride, $C_6$ to $C_{12}$ alcohols such as octanol; sulfonated oils; surface treated silica, precipitated silica, and fumed silica such as Aerosil® available from the Degussa Inc. of New York, N.Y. or mixtures thereof. One or more dry-feel modifiers can optionally be included in the emulsion in amounts ranging from 0.01 to about 20 weight %, preferably from about 0.5 to about 6 weight %.

Antimicrobial Preservative

An antimicrobial preservative is a substance or preparation which destroys, prevents or inhibits the multiplication/growth of microorganisms in the sunless tanning emulsion and may offer protection from oxidation. Preservatives are used to make self-sterilizing, aqueous based products such as emulsions. This is done to prevent the development of microorganisms that may be in the product from growing during manufacturing and distribution of the product and during use by consumers who may inadvertently contaminate the products during normal use. Typical preservatives include the lower alkyl esters of para-hydroxybenzoates (parabens) especially, methylparaben, propylparaben, isobutylparaben and mixtures thereof, benzyl alcohol and benzoic acid. A commercially available preservative is Germaben®II, composed of a mixture of diazolidinyl urea (30%), methylparaben (11%), propylparaben (3%) and propylene glycol (56%), trademark of Sutton Laboratories, Charlotte, N.C. One or more antimicrobial preservatives can optionally be included in the emulsion in an amount ranging from about 0.001 to about 10 weight percent, preferably about 0.05 to about 2 percent.

Thickening Agents

The viscosity of the emulsion may be maintained at a selected level using an acceptable thickening agent, such as methyl cellulose, xanthan gum carboxymethyl cellulose, hydroxpropyl cellulose, carbomer, carbopol, cetyl alcohol and the like. The thickening agent should be employed in amounts which will achieve the desired viscosity, and be used in amounts ranging from 0.01 to about 3% weight percent, preferably from 0.05 to about 2 percent, more preferably from about 0.1 to about 1 percent.

Antifoaming Agents

Antifoaming agents, also known as defoaming agents, are substance used to reduce foaming due to proteins, gases or nitrogenous materials which may interfere during processing. Examples include 2-octanol, sulfonated oils, organic phosphates, silicone fluids, dimethylpolysiloxane, etc. One defoaming agent is dimethicone, a mixture of methylated linear siloxane polymers, available as DC200 fluid, tradename of Dow Corning, Midland, Mich. The amount of anti-foaming agent which can be employed in the composition can range from about 0.1 to about 2 percent, more preferably from about 0.2 to about 0.5%.

Antioxidants

An antioxidant is a natural or synthetic substance added to the sunless tanning emulsion to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA)(usually as a mixture of ortho and meta isomers), butylated hydroxytoluene (BHT), nordihydroguaiaretic acid, vitamin E, vitamin E acetate, vitamin C and alkylated parabens such as methylparaben and propylparaben. One or more antioxidants can optionally be included in the emulsion in an amount ranging from about 0.001 to about 5 weight percent, preferably about 0.05 to about 2 percent.

Biological Additives

Biological additives are natural ingredients which have been isolated and/or puified, that have a cosmetic effect on the skin. Suitable biological additives include aloe vera, allantoin, hyaluronic acid, chitosan and chicory. The amounts of the biological additive in the composition can range from about 0.01 to about 10%, preferably from about 0.1 to about 2%.

Chelating Agents

Chelating agents are substances used to chelate or bind metallic ions with a certain heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the emulsion in amounts ranging from about 0.001 to about 0.1 weight percent.

Sunscreen Actives

Optionally, the composition of the present invention may contain a sunscreening effective amount of one or more oil-soluble or water-soluble sunscreening UV-B actives or a mixture of one or more UV-B actives and one or more UV-A actives. UV-A type sunscreening actives protect against long wavelength actinic radiation of the sun in the 320 to 400 nm range and UV-B type sunscreening actives protect against shorter wavelength, actinic radiation of the sun in the 290–320 nm range.

Typical sunscreen actives include trade name of para-aminobenzoic acid up to about 15 weight percent or from about 5 to 15% in admixture with other sunscreen actives; cinoxate up to about 3 weight percent or about 1 to 3% in admixture; diethanolamine methoxycinnamate up to 10 weight percent or about 8 to 10% in admixture; digalloyl trioleate up to 5 weight percent or about 2 to 5% in admixture; dioxybenzone up to 3 weight percent alone or in admixture; ethyl 4-[bis(hydroxypropyl)]aminobenzoate up to 5 weight percent or about 1 to 5% in admixture; glyceryl aminobenzoate up to 3 weight percent or about 2 to 3% in admixture; homosalate up to 15 weight percent or about 4 to 15% in admixture; lawsone up to 0.25 weight percent with dihydroxyacetone up to 3 weight percent; menthyl anthranilate up to 5 weight percent or about 3.5 to 5% in admixture; octocrylene up to 10 weight percent or 7 to about 10% in admixture; octyl methoxycinnamate up to 7.5 weight percent or about 2 to 7.5% in admixture; octyl salicylate up to 5 weight percent or about 3 to 5% in admixture; oxybenzone up to 6 weight percent or about 2 to 6% in admixture; padimate "O" up to 8 weight percent or about 1.4 to 8% in admixture; phenylbenzimidazole sulfonic acid up to 4 weight percent or about 1 to about 4% in admixture; red veterinary petrolatum up to 95 percent or about 30 to 95% in admixture; sulisobenzone up to 10 weight percent or about 5 to 10% in admixture; titanium dioxide up to 25 weight percent or about 2 to 25% in admixture; and trolamine salicylate up to 12 weight percent or about 5 to 12% in admixture.

Typical suitable UV-B type sunscreening actives include benzophenone-3, benzophenone-8, substituted para-aminobenzoates, e.g.,alkyl esters of para-methoxycinnamate, octyl methoxycinnamate and octyl para-methoxycinnamate, available from Givaudan Corp., Clifton, N.J. 07104 under the tradename Parsol MCX and usually present in the range of about 2 to 7.5 weight percent or or octyl salicylate available from Haarmann and Reimer, Springfield, N.J., 07081, usually in the range of about 3 to 5 weight percent. The amount of UV-B type sunscreening active should be sufficient to give an SPF of at least 2 to 15.

Typical suitable UV-A type sunscreening actives include oxybenzone and avobenzone, available from Givaudan Corp. as Parsol® 1789. The amount of UV-A type sunscreening active can range from about 2 to about 6 weight percent. Emulsions containing mixtures of UV-B and UV-A type sunscreen actives should be sufficient to provide an SPF of 2 to 50.

Except as noted otherwise, one or more sunscreen actives can be employed in the present emulsion in amounts up to 35 weight percent, preferably about 12 to about 30 weight percent of the sunscreen composition, more preferably from about 5 to about 15 weight percent.

Fragrances

Fragrances are aromatic compounds which can impart an aesthetically pleasing aroma to the sunless tanning emulsion. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent.

Dispensers

The colored, sunless tanning emulsions of the present invention containing the disappearing color indicator can be stored or dispensed in any container suitable for convenient delivery, i.e. pouring or spraying. Such containers can include but are not limited to jars, bottles, lotion pumps, pump spray bottles and aerosols.

EXAMPLE 1

Sunless Tanning Emulsion With Disappearing Color Indicator

| Ingredients | Theoretical Quantity (g) | Weight percent (%) |
| --- | --- | --- |
| Part A- Water soluble ingredients | | |
| Water | 56.08700 | 56.08700 |
| Glycerin | 5.00000 | 5.00000 |
| Brij 56 (Ceteth 10) | 1.18060 | 1.18000 |
| Aloe Vera Powder | 0.05000 | 0.05000 |
| Part B - Oil soluble ingredients | | |
| Promulgin G emulsifier | 6.50000 | 6.50000 |
| Isopropyl palmitate | 5.00000 | 5.00000 |
| Brij 52 (Ceteth-8) | 0.82000 | 0.82000 |
| Cetyl Alcohol | 0.30000 | 0.30000 |
| Vit E Acetate | 0.10000 | 0.10000 |
| DC200 fluid | 0.30000 | 0.30000 |
| Part C - Sunless Tanner | | |
| Water | 7.50000 | 7.50000 |
| Dihydroxyacetone (DHA) | 6.00000 | 6.00000 |
| Part D - Other Ingredients | | |
| Germaben II | 1.00000 | 1.00000 |
| Fragrance | 0.15000 | 0.15000 |
| Part E - Color Indicator | | |
| Water | 10.00000 | 10.00000 |
| Ext DC Violet #2 | 0.00285 | 0.00285 |
| Ext DC red #33 | 0.00015 | 0.00015 |
| FDC Yellow #6 Dye | 0.01000 | 0.01000 |

In a stainless steel pot, heat the water of Part A to about 75° C. and add remaining ingredients. Similarly admix the ingredients of Part B in a separate pot heated to about 75° C. Using vigorous stirring for at least 5 minutes, add Part B to Part A until an emulsion is formed and cool to 51° C. with slow mixing. At room temperature, uniformly admix the ingredients of Part C in a separate pot, add to the above emulsion and mix well. Add the ingredients of Part D to the above emulsion, mix well and cool. In a separate pot, admix the ingredients of Part E (containing a total of 0.013% color indicator), add to the above emulsion and mix well to give the sunless tanning emulsion a light brown color. The color indicator imparts the light brown color to the sunless tanning emulsion, enabling it to be readily visualized when the sunless tanning emulsion is initially applied to the skin. When the colored sunless tanning emulsion dries after it is spread on the skin and/or is rubbed out, the brown color substantially disappears.

EXAMPLE 2

Essentially the same ingredients and processing are employed as described in Example 1, except that 0.00570 g of the Ext DC Violet #2, 0.00030 g of the Ext DC red#33 (sub-totaling 0.006 g of a purple D&C Dye Blend) and 0.02000 g of the FDC Yellow #6 Dye (containing a total of 0.026% color indicator) are employed to give the sunless tanning emulsion a medium brown color.

EXAMPLE 3

Essentially the same ingredients and processing are employed as described in Example 1, except that 0.00855 g of the Ext DC Violet #2, 0.00045 g of the Ext DC red#33 (sub-totaling 0.009 g of a purple D&C Dye Blend) and 0.03000 g of the FDC Yellow #6 Dye (containing a total of 0.039% color indicator) are employed to give the sunless tanning emulsion a dark brown color.

The visualization and disappearance of the colored indicator on the skin can be evaluated using visual, chromatographic and pantone matching systems.

To evaluate the color indicator on the skin, it may be helpful to have an objective, instrumental measurement of colors and intensities. Accordingly, a method has been developed using a Minolta Chroma Meter CR-200, which uses reflected light from a surface and gives results in terms of the CIE (International Commission on Illumination) tristimulus values. These values are subsequently transformed mathematically into the $L^*$ $a^*$ $b^*$ color space, wherein the magnitudes of changes in hue and intensity of color correspond closely with those perceived by the human eye.

$L^*$, being achromatic, ranges from black ($L^*=0$) to white ($L^*=100$); this term is called "metric lightness" and is a measure of how light or dark a color is, relative to a matching shade of gray. Hue is measured in terms of the chromaticity coordinates $a^*$ and $b^*$, where $a^*$ indicates redness ($a^*>0$) and $b^*$ indicates yellowness ($b^*>0$). The values of $a^*$ and $b^*$ can be plotted with $a^*$ as the x-axis and $b^*$ as the y axis, to give quantitative color information: "metric chroma" is the length of a line from the origin ($a^*=0, b^*=0$) to the point of a sample reading, while 'metric hue angle, is the angle between the $a^*$ axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter can be used to measure a base line skin tone as well as residual color left on the skin after "rub out" with a number of subjects, to establish a target for disappearance of color applied to the skin.

What is claimed is:

1. A colored, sunless tanning emulsion comprising:
   a) at least one water-soluble dye that imparts a color other than white to the sunless tanning emulsion, such that when the sunless tanning emulsion dries after it is spread on the skin and/or is rubbed out, the color substantially disappears;
   b) at least one sunless tanner;
   c) at least one emulsfier; and
   d) sufficient water to form the colored emulsion.

2. The colored, sunless tanning emulsion of claim 1 wherein the water-soluble dye is an External DC color or blend of two or more External DC colors.

3. The colored, sunless tanning emulsion of claim 1 wherein the water-soluble dye imparts a brown color to the sunless tanning emulsion.

4. The colored, sunless tanning emulsion of claim 1 wherein the water-soluble dye is a blend of Ext DC violet #2, Ext DC red#33 and FDC Yellow #6.

5. The colored, sunless tanning emulsion of claim 1 wherein the amount of the water-soluble dye in the emulsion can range from about 0.00001 to about 0.5 % by weight of the emulsion.

6. The colored, sunless tanning emulsion of claim 1 wherein the amount of the water-soluble dye in the emulsion can range from about 0.0001 to about 0.2% by weight of the emulsion.

7. The colored, sunless tanning emulsion of claim 1 wherein the amount of the water-soluble dye in the emulsion can range from about 0.001 to about 0.1% by weight of the emulsion.

8. The colored, sunless tanning emulsion of claim 1 wherein the amount of the water-soluble dye in the emulsion is about 0.01 to about 0.05% by weight of the emulsion.

9. The colored, sunless tanning emulsion of claim 1 wherein the emulsion is an oil-in-water emulsion (o/w).

10. The colored, sunless tanning emulsion of claim 1 wherein the emulsion is an water-in-oil emulsion (w/o).

11. The colored, sunless tanning emulsion of claim 1 wherein the emulsion is an oil-in water-in oil emulsion (o/w/o).

12. The colored, sunless tanning emulsion of claim 1 wherein the emulsion is a water-in-oil-in water emulsion (w/o/w).

13. The colored, sunless tanning emulsion of claim 1 having a pH of about 2.5 to about 7.

14. The colored, sunless tanning emulsion of claim 1 having a pH of about 3 to about 5.5.

15. The colored, sunless tanning emulsion of claim 1 further comprising one or more emollients.

16. The colored, sunless tanning emulsion of claim 1 wherein the sunless tanner is dihydroxyacetone (DHA).

17. The colored, sunless tanning emulsion of claim 16 further comprising one or more antimicrobial preservatives.

18. The colored, sunless tanning emulsion of claim 17 further comprising one or more dry-feel modifiers.

19. The colored, sunless tanning emulsion of claim 18 further comprising one or more fragrances.

20. A method for more uniformly tanning the skin comprising topically applying to the skin the colored, sunless tanning emulsion of claim 1.

* * * * *